US012751943B2

(12) United States Patent
Lang et al.

(10) Patent No.: US 12,751,943 B2
(45) Date of Patent: Oct. 6, 2026

(54) INJECTABLE FORMULATIONS IN A METHOD FOR TREATING PAIN

(71) Applicant: PELTHOS THERAPEUTICS INC., Durham, NC (US)

(72) Inventors: Eric D. Lang, Plainsboro, NJ (US); Simon Paul Chandler, Warwick, RI (US); Deshou Jiang, Belle Mead, NJ (US); Richard Malamut, Philadelphia, PA (US)

(73) Assignee: PELTHOS THERAPEUTICS INC., Durham, NC (US)

( * ) Notice: Subject to any disclaimer, the term of this patent is extended or adjusted under 35 U.S.C. 154(b) by 0 days.

(21) Appl. No.: 19/365,336

(22) Filed: Oct. 22, 2025

(65) Prior Publication Data

US 2026/0108499 A1 Apr. 23, 2026

Related U.S. Application Data

(60) Provisional application No. 63/747,797, filed on Jan. 21, 2025, provisional application No. 63/710,647, filed on Oct. 23, 2024.

(51) Int. Cl.

| | |
|---|---|
| ***A61K 31/426*** | (2006.01) |
| ***A61K 9/00*** | (2006.01) |
| ***A61K 9/06*** | (2006.01) |
| ***A61K 9/08*** | (2006.01) |
| ***A61K 9/50*** | (2006.01) |

(Continued)

(52) U.S. Cl.

CPC .......... *A61K 31/426* (2013.01); *A61K 9/0019* (2013.01); *A61K 9/06* (2013.01); *A61K 9/08* (2013.01); *A61K 9/5031* (2013.01); *A61K 47/02* (2013.01); *A61K 47/10* (2013.01); *A61K 47/14* (2013.01); *A61K 47/24* (2013.01);

(Continued)

(58) Field of Classification Search

CPC ............ A61P 1/14; A61P 19/02; A61P 19/04; A61P 21/00; A61P 25/02; A61P 25/04; A61P 29/00; A61P 43/00; C07D 277/52; C07D 285/08; C07D 417/12; C07D 487/00

See application file for complete search history.

(56) References Cited

U.S. PATENT DOCUMENTS

| | | | |
|---|---|---|---|
| 9,458,118 | B2 | 10/2016 | Babich et al. |
| 2017/0304306 | A1 | 10/2017 | Wang-Fischer et al. |

FOREIGN PATENT DOCUMENTS

| | | | |
|---|---|---|---|
| WO | WO-2015/038533 A2 | 3/2015 | |
| WO | WO 2019/217822 A1 | 11/2019 | |

(Continued)

OTHER PUBLICATIONS

Pramanick et al. (Pharm times, vol. 45 , No. 3, Mar. 2013 (65-77) (Year: 2013).*

(Continued)

*Primary Examiner* — Savitha M Rao
(74) *Attorney, Agent, or Firm* — Myers Bigel, P.A.

(57) ABSTRACT

The present invention relates to pharmaceutical formulations comprising 2-{[3-(5-chloro-2-{2-chloro-5-fluoro-4-[(1,3-thiazol-4-yl) sulfamoyl]phenoxy}phenyl)propyl]amino}acetamide, or a pharmaceutically acceptable salt thereof, for extended release, to methods for preparation thereof, and to uses thereof for treatment of pain or providing peri-operative anesthesia or post-operative analgesia.

7 Claims, 5 Drawing Sheets

(51) Int. Cl.

| | |
|---|---|
| ***A61K 47/02*** | (2006.01) |
| ***A61K 47/10*** | (2017.01) |
| ***A61K 47/14*** | (2017.01) |
| ***A61K 47/24*** | (2006.01) |
| ***A61K 47/32*** | (2006.01) |
| ***A61K 47/38*** | (2006.01) |
| ***A61K 47/44*** | (2017.01) |
| ***A61P 25/04*** | (2006.01) |

(52) U.S. Cl.
CPC .............. *A61K 47/32* (2013.01); *A61K 47/38* (2013.01); *A61K 47/44* (2013.01); *A61P 25/04* (2018.01)

(56) References Cited

FOREIGN PATENT DOCUMENTS

| | | | |
|---|---|---|---|
| WO | WO 2022/178018 | A1 | 8/2022 |
| WO | WO 2024/089046 | A1 | 5/2024 |

OTHER PUBLICATIONS

Ahuja et al., "Topical Ocular Delivery of NSAIDs", The AAPS Journal, 2008, vol. 10, No. 2, pp. 229-241.

Baranowski, et al., "Ophthalmic Drug Dosage Forms: Characterisation and Research Methods", The Scientific World Journal, vol. 2014, Article ID 861904, pp. 2-14.

Delwig, et al., "Evaluation of Selective $Na_v$1.7 Inibitors for the Treatment of Ocular Pain", Investigative Ophthalmology & Visual Science, Jul. 2018, vol. 59, 2679.

Delwig, et al., "Nav1.7 inibitors relieve ocular discomfort in a rat model of dry eye disease", Investigative Ophthalmology & Visual Science, Jun. 2020, vol. 61, 143.

Jansook et al., "Aqueous Prostaglandin Eye Drop Formulations", Pharmaceutics 2022, 14, 2142, pp. 2-13.

International Search Report from corresponding International Application No. PCT/US2025/052019 dated Jan. 21, 2026.

International Search Report from corresponding International Application No. PCT/US2025/052033 dated Mar. 2, 2026.

* cited by examiner

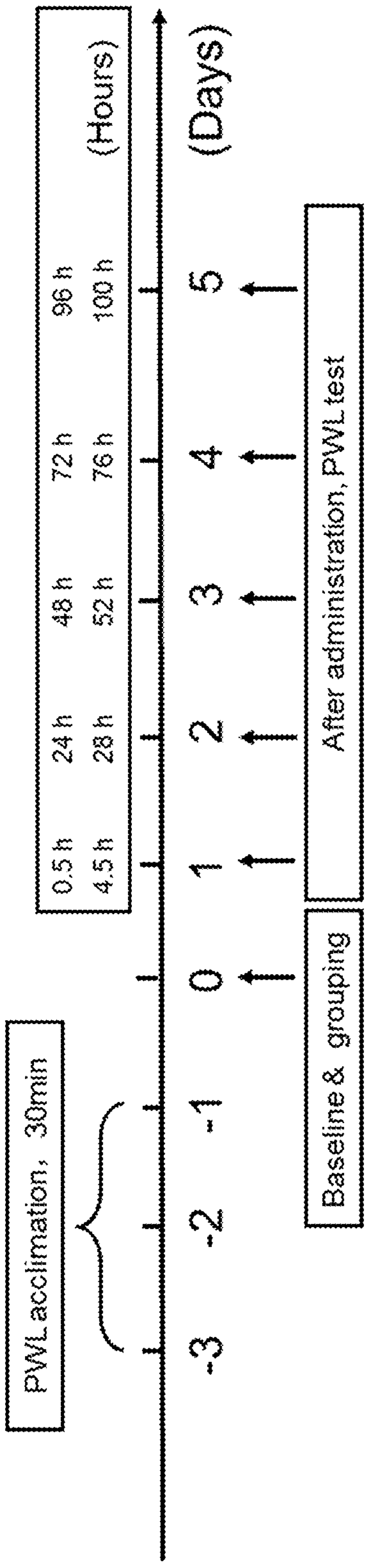
Figure 5A: Scheme 1
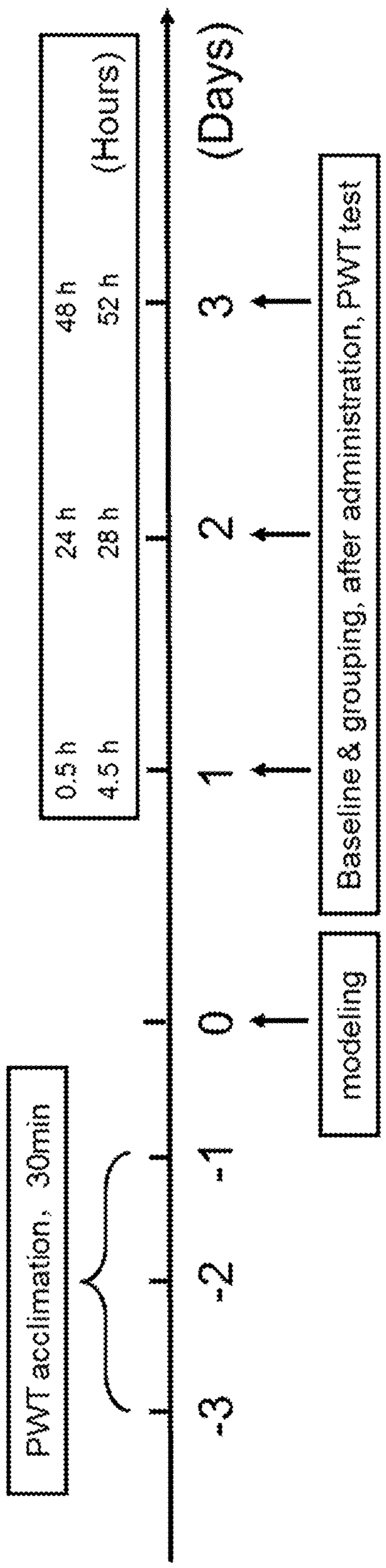
Figure 5B: Scheme 2

INJECTABLE FORMULATIONS IN A METHOD FOR TREATING PAIN

CROSS REFERENCE TO RELATED APPLICATIONS

This application claims the benefit of U.S. Provisional Patent Application No. 63/710,647, filed Oct. 23, 2024, and U.S. Provisional Patent Application No. 63/747,797, filed Jan. 21, 2025, both of which are incorporated herein by reference in their entirety.

FIELD OF THE INVENTION

The present invention relates to pharmaceutical formulations comprising 2-{[3-(5-chloro-2-{2-chloro-5-fluoro-4-[(1,3-thiazol-4-yl) sulfamoyl]phenoxy}phenyl) propyl] amino}acetamide, or a pharmaceutically acceptable salt thereof, for extended release, to methods for preparation thereof, and to uses thereof for treatment of pain or providing peri-operative anesthesia or post-operative analgesia.

BACKGROUND OF THE INVENTION

Pain conditions affect a substantial number of U.S. populations annually in direct medical treatment costs and lost productivity. Treatment options typically provide only partial pain relief and are limited by inconvenient dosing and by side effects, e.g., somnolence, ataxia, edema, gastrointestinal discomfort, and respiratory depression.

Compound 2-{[3-(5-chloro-2-{2-chloro-5-fluoro-4-[(1,3-thiazol-4-yl) sulfamoyl]phenoxy}phenyl) propyl] amino}acetamide) has been found to be able to address the shortcomings of the available options for treatment of pain or providing peri-operative anesthesia or post-operative analgesia.

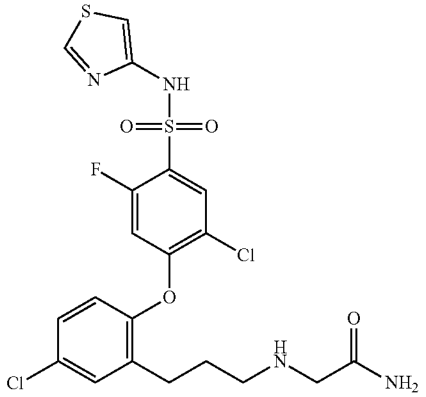 [SMILES: NC(=O)CNCCCc1cc(Cl)ccc1Oc1cc(F)c(S(=O)(=O)Nc2cscn2)cc1Cl]

(2-{[3-(5-chloro-2-{2-chloro-5-fluoro-4-[(1,3-thiazol-4-yl) sulfamoyl]phenoxy}phenyl) propyl]amino}acetamide)

2-{[3-(5-chloro-2-{2-chloro-5-fluoro-4-[(1,3-thiazol-4-yl)sulfamoyl]phenoxy}phenyl) propyl]amino}acetamide and its salts (e.g., hydrochloride salt) are low in solubility in both aqueous and oil phases. There is a need in the field to develop and provide desired formulations with high concentrations that may provide a therapeutic effective amount of the active ingredient over an extended period of time for the treatment of pain or providing peri-operative anesthesia or post-operative analgesia with reduced or zero side effects.

SUMMARY OF THE INVENTION

In one aspect, the present invention provides a pharmaceutical injectable formulation comprising an active ingredient and a pharmaceutically acceptable surfactant, suspending agent, buffer, osmolality adjuster, viscosity adjuster, solubilizer, solvent, preservative, matrix, or carrier, or any combination thereof, wherein the active ingredient is Compound A, (A)

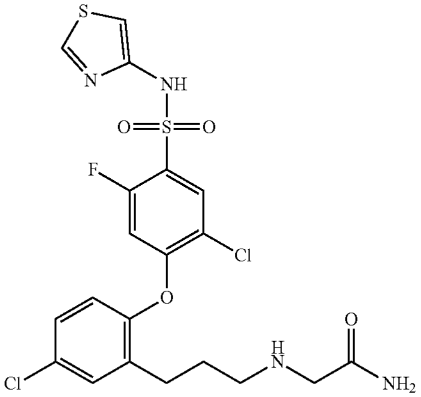

or a pharmaceutically acceptable salt thereof, wherein the concentration of Compound A, or a pharmaceutically acceptable salt thereof, is about 1 mg/mL-200 mg/mL.

In some embodiments, the pharmaceutical injectable formulation is an aqueous suspension formulation. In some embodiments, the aqueous suspension formulation of the invention comprises about 50 mg/mL HCl salt of Compound A, about 0.5% (w/w) poloxamer 188, about 1% (w/w) CMC-Na, about 0.6% (w/w) NaCl, a pH of about 7.4 in about 20 mM phosphate buffer

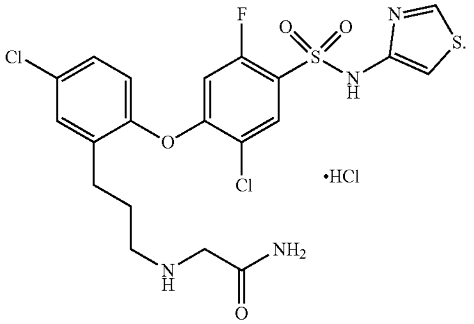 [SMILES: NC(=O)CNCCCc1cc(Cl)ccc1Oc1cc(F)c(S(=O)(=O)Nc2cscn2)cc1Cl ; Cl]

In a further aspect, the present invention provides a pharmaceutical injectable formulation, wherein the pharmaceutical injectable formulation is a poly(lactic-co-glycolic acid) (PLGA) microsphere formulation. In some embodiments, the PLGA microsphere formulation comprises Compound A (about 50 mg/mL), PLGA, about 1% (w/w) CMC-Na, about 1.5% (w/w) mannitol, and a pH of about 7.4 in about 20 mM phosphate buffer, wherein the weight ratio of Compound A to PLGA is about 1:2.

In a further aspect, the present invention provides a pharmaceutical injectable formulation, wherein the pharmaceutical injectable formulation is an oil suspension formulation. In certain embodiments, the oil suspension formulation comprises the HCl salt of Compound A (about 50 mg/mL) and benzyl benzoate in sesame oil, wherein the concentration of benzyl benzoate is about 20% (v/v).

In one aspect, the present invention provides a pharmaceutical injectable formulation, wherein the injectable formulation is an in-situ gel formulation. In some embodiments, the in-situ gel formulation comprises about 100 mg/mL HCl salt of Compound A (9.5% w/w), about 24.40% (w/w) NMP, soy lecithin, and glycerin dioleate, wherein the weight ratio of soy lecithin and glycerin dioleate is about 40:60.

In a further aspect, the present invention provides a method for treating or alleviating pain or providing perioperative anesthesia or post-operative analgesia, comprising administering to a subject in need thereof a therapeutically effective amount of a pharmaceutical injectable formulation of the invention as described anywhere herein.

These and other aspects of the invention will be appreciated from the ensuing descriptions of the figures and detailed description of the invention.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIGS. 5A and 5B depict Scheme 1 and Scheme 2 related to Example 4.

Figure 1:
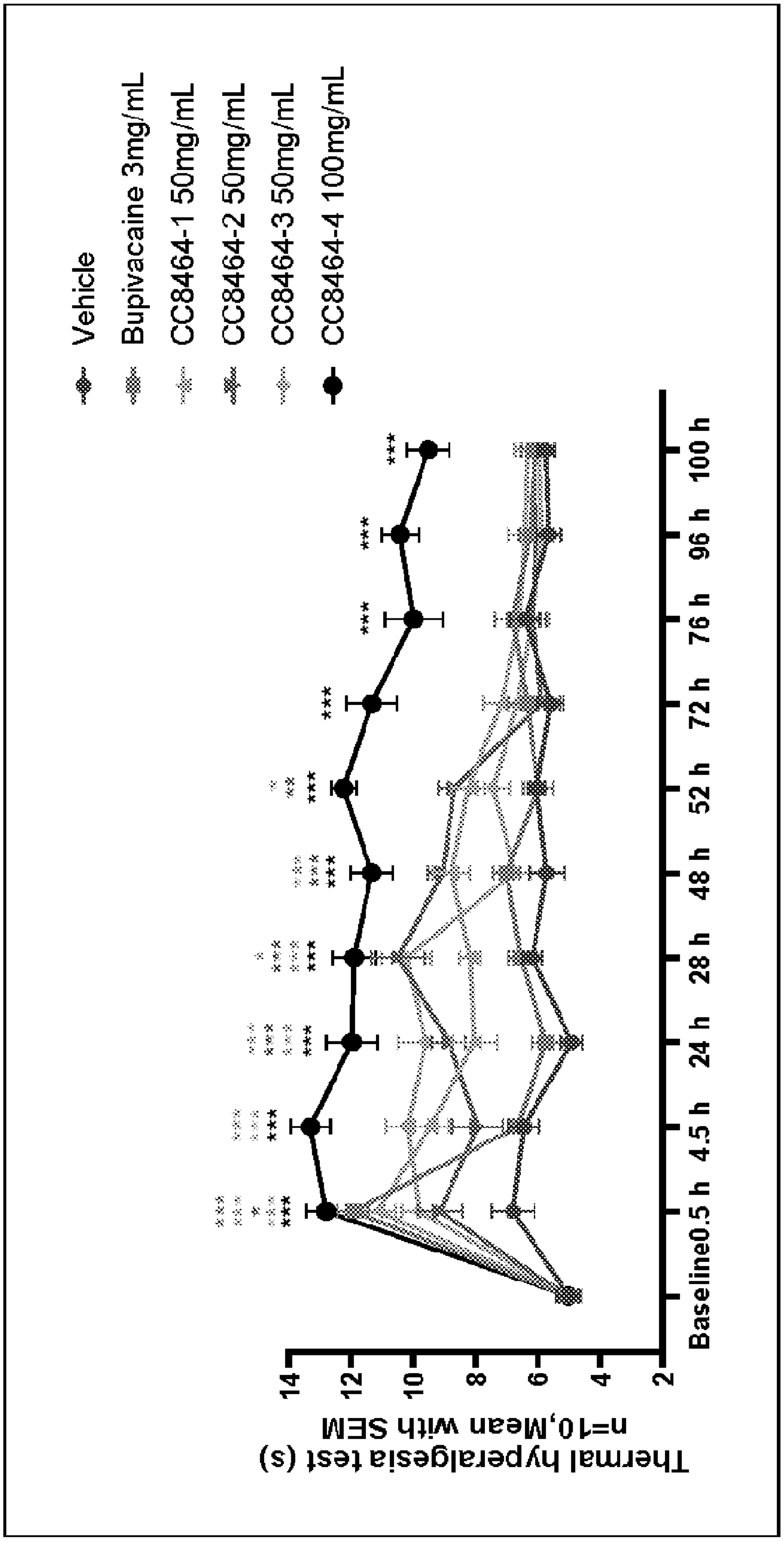
FIG. 1 depicts thermal hyperalgesia test results in Example 4.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

The present invention provides a pharmaceutical injectable formulation comprising 2-{[3-(5-chloro-2-{2-chloro-5-fluoro-4-[(1,3-thiazol-4-yl) sulfamoyl]phenoxy}phenyl) propyl]amino}acetamide (Compound A), or a pharmaceutically acceptable salt thereof, for example, an aqueous suspension formulation, a PLGA microsphere formulation, an oil suspension formulation, and an in-situ gel formulation. The formulation of the invention can be used for the treatment of pain with reduced or zero side effects and with unexpected advantages. For example, when used for a nerve block in post operative pain (e.g., knee surgery or shoulder surgery or any other surgery where a peripheral nerve block is standard of care to provide anesthesia), the formulation of the invention has demonstrated the advantage of providing analgesia without paralyzing the muscles, which would allow movement which is important after surgery. Further, the formulation of the invention can be used as an intraarticular injection (e.g., knee) for the treatment of pain due to osteoarthritis or due to focal peripheral neuropathic pain and potentially for its disease modifying effects (e.g., increases in cartilage volume), particularly when the release profile is prolonged.

In one aspect, the present invention provides a pharmaceutical injectable formulation comprising an active ingredient and a pharmaceutically acceptable surfactant, suspending agent, buffer, osmolality adjuster, viscosity adjuster, solubilizer, solvent, preservative, matrix, or carrier, or any combination thereof, wherein the active ingredient is Compound A, (A)

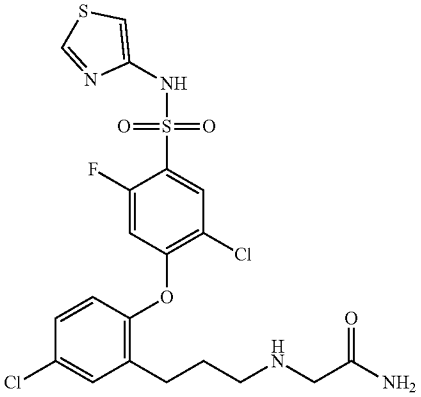

or a pharmaceutically acceptable salt thereof.

In some embodiments, the concentration of Compound A, or a pharmaceutically acceptable salt thereof, is about 1 mg/mL-200 mg/mL.

In other embodiments, the concentration of Compound A, or a pharmaceutically acceptable salt thereof (e.g., a hydrochloride salt), in the injectable formulation of the invention (e.g., the aqueous suspension formulation, the PLGA microsphere formulation, the oil suspension formulation, or the in-situ gel formulation) is from about 1 mg/mL to about 50 mg/mL, from about 50 mg/mL to about 100 mg/mL, from about 1 mg/mL to about 20 mg/mL, from about 20 mg/mL to about 100 mg/mL, from about 20 mg/mL to about 150 mg/mL, from about 20 mg/mL to about 200 mg/mL, from about 20 mg/mL to about 300 mg/mL, from about 20 mg/mL to about 450 mg/mL, from about 20 mg/mL, to about 500 mg/mL, from about 20 mg/mL to about 750 mg/mL, or/and from about 20 mg/mL to about 1000 mg/mL.

In some embodiments, the concentration of Compound A, or a pharmaceutically acceptable salt thereof (e.g., a hydrochloride salt), in the injectable formulation of the invention (e.g., the aqueous suspension formulation, the PLGA microsphere formulation, the oil suspension formulation, or the in-situ gel formulation) is about 1 mg/mL, 1.5 mg/mL, 2 mg/mL, 2.5 mg/mL, 3 mg/mL, 3.5 mg/mL, 4 mg/mL, 4.5 mg/mL, 5 mg/mL, 5.5 mg/mL, 6 mg/mL, 6.5 mg/mL, 7 mg/mL, 7.5 mg/mL, 8 mg/mL, 8.5 mg/mL, 9 mg/mL, 9.5 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 25 mg/mL, 26 mg/mL, 27 mg/mL, 28 mg/mL, 29 mg/mL, 30 mg/mL, 35 mg/mL, 40 mg/mL, 45 mg/mL, or 50 mg/mL.

In some embodiments, the concentration of Compound A, or a pharmaceutically acceptable salt thereof (e.g., a hydrochloride salt), in the injectable formulation of the invention (e.g., the aqueous suspension formulation, the PLGA microsphere formulation, the oil suspension formulation, or the in-situ gel formulation) is about 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 110 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 375 mg/mL, or 400 mg/mL.

In other embodiments, the concentration of Compound A, or a pharmaceutically acceptable salt thereof (e.g., a hydrochloride salt), in the injectable formulation of the invention (e.g., the aqueous suspension formulation, the PLGA microsphere formulation, the oil suspension formulation, or the in-situ gel formulation) is about 60 mg/mL, 70 mg/mL, 80 mg/mL, 90 mg/mL, 100 mg/mL, 110 mg/mL, 120 mg/mL, 125 mg/mL, 200 mg/mL, 250 mg/mL, 300 mg/mL, 450 mg/mL, 500 mg/mL, 600 mg/mL, 900 mg/mL, or 1000 mg/mL.

In some embodiments of the injectable formulation of the invention, the active ingredient is Compound A in its free base form. In other embodiments, Compound A can be in the form of a pharmaceutically acceptable salt. Accordingly, in some embodiments, the active ingredient is a pharmaceutically acceptable salt of Compound A. In some embodiments, the pharmaceutically acceptable salt of Compound A is of Compound A and an acid selected from the group consisting of acetic acid, benzoic acid, citric acid, dichloroacetic acid, fumaric acid, HCl, $HBF_4$, succinic acid, L-tartaric acid, maleic acid, $H_2SO_4$, HBr, $H_3PO_4$, 1,5-naphthalenedisulfonic acid, benzenesulfonic acid, dibenzoyl-d-tartaric acid, oxalic acid, R-mandelic acid, salicylic acid, methanesulfonic acid, p-toluenesulfonic acid, s-camphorsulfonic acid, TFA, ethanesulfonic acid. In some embodiments, the pharmaceutically acceptable salt of Compound A is of Compound A and an acid selected from the group consisting of hydrochloride acid, hydrobromic acid, and sulfuric acid. In certain embodiments, the active ingredient of the pharmaceutical injectable formulation is a hydrochloride salt of Compound A.

As used herein, the terms “Compound A”, “Compound A free base”, “Compound A in its free base form”, and “free base of Compound A” are used interchangeably. In some embodiments, such terms are used to differentiate from the term “salt of Compound A”, “salt form of Compound A”, or “Compound A HCl salt”.

In some embodiments, as used herein, the term “CC8464” is meant for Compound A, while the term “CC8464 HCl” is meant for a “HCl salt of Compound A” or “hydrochloride salt of Compound A”.

As used herein, Compound A or a hydrochloride salt of Compound A can be prepared by any methods known in the art, e.g., as those described in PCT Patent Publication No. WO 2015/038533.

In one embodiment, the pharmaceutical injectable formulation is an aqueous suspension formulation. In some embodiments of the aqueous suspension formulation, the active ingredient is a HCl salt of Compound A

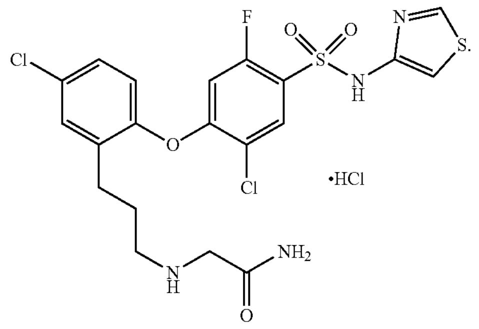 [SMILES: NC(=O)CNCCCc1cc(Cl)ccc1Oc1cc(F)c(S(=O)(=O)Nc2cscn2)cc1Cl ; Cl]

In some embodiments, the concentration of the HCl salt of Compound A is about 1 mg/mL-200 mg/mL. In other embodiments, the concentration of the HCl salt of Compound A is about 50 mg/mL.

In some embodiments of the aqueous suspension formulation of the invention, the surfactant is poloxamer 188. In certain embodiments, the concentration of the surfactant is about 0.5% (w/w). In some embodiments, the suspending agent is sodium carboxymethylcellulose (CMC-Na). In some embodiments, the concentration of the suspending agent is about 1% (w/w). In some embodiments, the buffer comprises disodium hydrogen phosphate dihydrate. In some embodiments, the buffer comprises sodium dihydrogen phosphate dihydrate. In some embodiments, the buffer comprises disodium hydrogen phosphate dihydrate and sodium dihydrogen phosphate dihydrate. In some embodiments, the osmolality adjuster is sodium chloride. In some embodiments, the concentration of the osmolality adjuster is about 0.6% (w/w). In some embodiments, the pH of the aqueous suspension formulation is from about 6.0 to about 7.5. In other embodiments, the pH of the aqueous suspension formulation is about 7.4.

In some embodiments, the aqueous suspension formulation of the invention comprises about 50 mg/mL HCl salt of Compound A, about 0.5% (w/w) poloxamer 188, about 1% (w/w) CMC-Na, about 0.6% (w/w) NaCl, a pH of about 7.4 in about 20 mM phosphate buffer.

In another aspect, the present invention provides a kit suitable for preparing a pharmaceutical injectable formulation of the invention, wherein the formulation is an aqueous suspension formulation, said kit comprising (i) a first container comprising a HCl salt of Compound A having a $D_{90}$ particle size of less than 15 μm, and (ii) a second container comprising the pharmaceutically acceptable surfactant, suspending agent, buffer, osmolality adjuster, viscosity adjuster, solubilizer, solvent, preservative, matrix, or carrier, or any combination.

In another aspect, the present invention provides a method for preparing a pharmaceutical injectable formulation of the invention, wherein the formulation is an aqueous suspension formulation, comprising (i) providing a first container comprising a HCl salt of Compound A, (ii) providing a second container comprising a mixture of 0.5% (w/w) poloxamer 188, 1% (w/w) CMC-Na, and 0.6% (w/w) NaCl in 20 mM phosphate buffer (pH 7.4), and (iii) re-suspending the HCl salt of Compound A from the first container with the mixture from the second container and sonicating to prepare the aqueous suspension formulation of HCl salt of Compound A.

In some embodiments, the method of the invention for preparing the aqueous suspension formulation comprises, prior to Step (i), a step of milling a HCl salt of Compound A. In some embodiments, the step of milling provides a HCl salt of Compound A having a $D_{90}$ particle size of less than 15 μm.

In some embodiments of the method of the invention, the HCl salt of Compound A in the aqueous suspension formulation has a concentration of about 1 mg/mL-200 mg/mL. In other embodiments, the HCl salt of Compound A in the aqueous suspension formulation has a concentration of about 50 mg/mL.

In some embodiments, the aqueous suspension formulation prepared by the method of the invention comprises about 50 mg/mL HCl salt of Compound A, about 0.5% (w/w) poloxamer 188, about 1% (w/w) CMC-Na, about 0.6% (w/w) NaCl, a pH of about 7.4 in about 20 mM phosphate buffer.

In a further aspect, the present invention provides a pharmaceutical injectable formulation, wherein the pharmaceutical injectable formulation is a poly(lactic-co-glycolic acid) (PLGA) microsphere formulation. In some embodiments, the active ingredient in the PLGA microsphere formulation is Compound A in its free base form, and wherein the concentration of Compound A is about 50 mg/mL. In some embodiments, the weight ratio of Compound A to PLGA is about 1:0.5, 1:1, 1:2, 1:3, 2:1, or 3:1. In certain embodiments, the weight ratio of Compound A to PLGA is 1:2. In some embodiments, the osmolality adjuster is mannitol. In certain embodiments, the concentration of the osmolality adjuster is about 1.5% (w/w). In some embodiments, the suspending agent is sodium carboxymethylcellulose (CMC-Na). In certain embodiments, the concentration of the suspending agent is about 1% (w/w). In some embodiments, the buffer comprises disodium hydrogen phosphate dihydrate. In other embodiments, the buffer comprises sodium dihydrogen phosphate dihydrate. In certain embodiments, the buffer comprises disodium hydrogen phosphate dihydrate and sodium dihydrogen phosphate dihydrate. In some embodiments, the pH of the PLGA microsphere formulation is from about 6.0 to about 7.5. In certain embodiments, the pH of the PLGA microsphere formulation is about 7.4.

In some embodiments, the PLGA microsphere formulation comprises Compound A (about 20 mg/mL), PLGA, about 1% (w/w) CMC-Na, about 1.5% (w/w) mannitol, and a pH of about 7.4 in about 20 mM phosphate buffer, wherein the weight ratio of Compound A to PLGA is about 1:2.

In some embodiments, the present invention provides a kit suitable for preparing a pharmaceutical formulation, wherein the formulation is a PLGA microsphere formulation, said kit comprising (i) a first container comprising Compound A, a carrier, and an osmolality adjuster, and (ii) a second container comprising the surfactant, suspending agent, buffer, osmolality adjuster, viscosity adjuster, solubilizer, solvent, preservative, matrix, or carrier, or any combination.

In some embodiments, the present invention provides a method for preparing a pharmaceutical injectable formulation, wherein he pharmaceutical injectable formulation is a PLGA microsphere formulation of Compound A, comprising (i) providing a first container comprising a PLGA microsphere lyophilized powder of Compound A, (ii) providing a second container comprising a vehicle of 1% CMC-Na and 1.5% Mannitol in 10 mM phosphate buffer (pH 7.4), and (iii) re-suspending the PLGA microsphere lyophilized powder of Compound A from the first container with the vehicle from the second container to provide the PLGA microsphere formulation of Compound A.

In some embodiments, the PLGA microsphere lyophilized powder of Compound A of the first container is prepared by a process comprising (a) providing an oil phase comprising Compound A and PLGA in an organic solvent; wherein the organic solvent comprises DCM and DMF in a volume ratio of about 1:1, (b) mixing and homogenizing the oil phase from step (a) with a water phase (1% PVA+0.9% NaCl in 20 mM phosphate buffer pH 8), followed by removing all liquid to yield a residual solid, (c) re-suspending the residual solid with 10 mM phosphate buffer (pH 7.4) and removing the supernatant, (d) repeating step (c) for 1-5 times, and (e) re-suspending the residual solid of step (d) with 10% mannitol in 20 mM phosphate buffer (pH 7.4) and freeze-dried to provide a PLGA microsphere lyophilized powder of Compound A.

In some embodiments, the vehicle of the second container is prepared by mixing CMC-Na, $Na_2HPO_4 \cdot 2H_2O$, $NaH_2PO_4 \cdot 2H_2O$, mannitol, and water, with a pH of about 7.4 adjusted with 1N HCl or 1N NaOH.

In some embodiments, Compound A in the PLGA microsphere formulation has a concentration of about 50 mg/mL.

In a further aspect, the present invention provides a pharmaceutical injectable formulation, wherein the pharmaceutical injectable formulation is an oil suspension formulation. In some embodiments, the active ingredient in the oil suspension formulation is a HCl salt of Compound A, and wherein the concentration of the HCl salt of Compound A is about 50 mg/mL.

In some embodiments of the oil suspension formulation of the invention, the solvent is sesame oil. In some embodiments, the preservative is benzyl benzoate. In certain embodiments, the oil suspension formulation comprises the HCl salt of Compound A (about 50 mg/mL) and benzyl benzoate in sesame oil, wherein the concentration of benzyl benzoate is about 20% (v/v).

In yet another aspect, the present invention provides a method for preparing a pharmaceutical injectable formulation, wherein the pharmaceutical injectable formulation is an oil suspension formulation, the method comprising mixing sesame oil, benzyl benzoate, and a HCl salt of Compound A, followed by homogenizing the resulting mixture to prepare the oil suspension formulation of a HCl salt of Compound A. In some embodiments, the HCl salt of Compound A is jet/ball milled prior to the step of mixing. In some embodiments, the jet/ball milling provides the HCl salt of Compound having a $D_{90}$ particle size of less than 15 μm.

In one aspect, the present invention provides a pharmaceutical injectable formulation, wherein the injectable formulation is an in-situ gel formulation. In some embodiments, the active ingredient of the in-situ gel formulation is a HCl salt of Compound A, and wherein the concentration of the HCl salt of Compound A is about 1 mg/mL-100 mg/mL. In some embodiments, the concentration of the HCl salt of Compound A is about 100 mg/mL. In some embodiments, the solvent is N-methylpyrrolidone (NMP). In some embodiments, the matrix comprises soy lecithin. In some embodiments, the matrix comprises glycerin dioleate. In some embodiments, the matrix comprises soy lecithin and glycerin dioleate.

In some embodiments, the in-situ gel formulation of the invention comprises about 100 mg/mL HCl salt of Compound A (9.5% w/w), about 24.40% (w/w) NMP, soy lecithin, and glycerin dioleate, wherein the weight ratio of soy lecithin and glycerin dioleate is about 40:60.

In some embodiments, the present invention provides a method for preparing a pharmaceutical injectable formulation, wherein the formulation is an in-situ gel formulation, comprising (i) providing a solution of a HCl salt of Compound A in NMP, and (ii) dissolving soy lecithin in the solution of step (i) and stirring, followed by adding glycerin dioleate and filtering to prepare the in-situ gel formulation of the HCl salt of Compound A.

The present invention provides a pharmaceutical formulation comprising Compound A, or a pharmaceutically acceptable salt thereof, for injection with extended releases. It is surprising that the pharmaceutical injectable formulations of the invention prolong the delivery of the active ingredient and enhance the duration of action of the treatment of pain in a subject in need thereof and potentially reduce associated adverse events and hence enhance safety profile.

In some embodiments, the injectable formulation of the invention, e.g., the aqueous suspension formulation, the PLGA microsphere formulation, the oil suspension formulation, and the in-situ gel formulation as described herein, releases the active ingredient, e.g., Compound A or a pharmaceutically acceptable salt thereof (e.g., a hydrochloride salt of Compound A), for at least 1-30 days. In some embodiments, the injectable formulation of the invention releases the active ingredient for at least 1-10 days. In some embodiments, the injectable formulation of the invention releases the active ingredient for at least 2-10 days. In some embodiments, the injectable formulation of the invention releases the active ingredient for at least 3-10 days. In other embodiments, the injectable formulation of the invention releases the active ingredient for 96 hours (3~5 days). In some embodiments, the injectable formulation of the invention releases the active ingredient for 24 hours.

In some embodiments, the injectable formulation of the invention releases the active ingredient for at least 2 days, at least 3 days, at least 5 days, at least 7 days, or at least 10 days. In some embodiments, the injectable formulation of the invention releases the active ingredient for at least 15 days, at least 20 days, at least 25 days, or at least 30 days. In some embodiments, the injectable formulation of the invention releases the active ingredient for at least 3 days. In other embodiments, the injectable formulation of the invention can sustain release for 96 hours (3~5 days).

In one aspect, the present invention provides an aqueous suspension formulation comprising about 50 mg/mL Compound A or a HCl salt of Compound A, about 0.5% (w/w) poloxamer 188, about 1% (w/w) CMC-Na, about 0.6% (w/w) NaCl, a pH of about 7.4 in about 20 mM phosphate buffer. In some embodiments, the formulation comprises a HCl salt of Compound A. In certain embodiments, the formulation comprises Compound A.

In one aspect, the present invention provides a PLGA microsphere formulation comprising about 20 mg/mL Compound A or a HCl salt of Compound A, poly(Lactic-co-Glycolic Acid (PLGA), about 1% (w/w) CMC-Na, about 1.5% (w/w) mannitol, and a pH of about 7.4 in about 20 mM phosphate buffer, wherein the weight ratio of Compound A to PLGA is about 1:2. In some embodiments, the formulation comprises a HCl salt of Compound A. In certain embodiments, the formulation comprises about 20 mg/mL Compound A.

In one aspect, the present invention provides an oil suspension formulation comprising about 50 mg/mL Compound A or a HCl salt of Compound A and benzyl benzoate in sesame oil, wherein the concentration of benzyl benzoate is about 20% (v/v). In some embodiments, the formulation comprises a HCl salt of Compound A. In certain embodiments, the formulation comprises Compound A.

In one aspect, the present invention provides an in-situ gel formulation comprising about 100 mg/mL Compound A or a HCl salt of Compound A, about 24.40% (w/w) NMP, about 26.4% (w/w) soy lecithin, and 39.6% (w/w) glycerin dioleate. In some embodiments, the formulation comprises a HCl salt of Compound A. In certain embodiments, the formulation comprises Compound A.

It is another aspect of the present invention that the injectable formulation with extended releases as described herein contains a high load or concentration of the active ingredient, e.g., Compound A or a pharmaceutically acceptable salt thereof.

In some embodiments, the present invention provides a peripheral nerve injection formulation comprising 20 mg/mL Compound A or above. In some embodiments, the present invention provides a peripheral nerve injection formulation comprising 50 mg/mL Compound A. In some embodiments the injectable formulation of the invention can sustain release for 96 hours (3~5 days). In some embodiments, the peripheral nerve injection formulation is a pharmaceutical injectable formulation of the invention described anywhere herein.

In some embodiments, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the "pharmaceutically acceptable salt" or "pharmaceutically acceptable salts" refers to derivatives of Compound A wherein the parent compound is modified by converting an existing base moiety to its salt form.

In some embodiments, the pharmaceutically acceptable salt of Compound A is formed from suitable non-toxic organic or inorganic acids including, but are not limited to, inorganic acids such as hydrochloric acid, hydrobromic acid, phosphoric acid, or sulfuric acid, and perchloric acid, or with organic acids such as acetic acid, oxalic acid, maleic acid, tartaric acid, citric acid, succinic acid, or malonic acid. In some embodiments, the pharmaceutically acceptable salt is of Compound A and an acid selected from the group consisting of acetic acid, benzoic acid, citric acid, dichloroacetic acid, fumaric acid, HCl, $HBF_4$, succinic acid, L-tartaric acid, maleic acid, $H_2SO_4$, HBr, $H_3PO_4$, 1,5-naphthalenedisulfonic acid, benzenesulfonic acid, dibenzoyl-d-tartaric acid, oxalic acid, R-mandelic acid, salicylic acid, methanesulfonic acid, p-toluenesulfonic acid, s-camphorsulfonic acid, TFA, ethanesulfonic acid.

In some embodiments, the pharmaceutically acceptable salt of a compound of formula A is a hydrochloride, hydrobromide, or sulfate salt. In one embodiment, the pharmaceutically acceptable salt of the compound of formula A is a hydrochloride salt.

It is another aspect of the present invention that the pharmaceutical injectable formulation of the invention as described anywhere herein can be used for treating or alleviating pain or providing peri-operative anesthesia or post-operative analgesia, Thus, in a further aspect, the present invention provides a method for treating or alleviating pain or providing peri-operative anesthesia or post-operative analgesia, comprising administering to a subject in need thereof a therapeutically effective amount of a pharmaceutical injectable formulation of the invention as described anywhere herein. In some embodiments, the pharmaceutical injectable formulation of the invention is an aqueous suspension formulation, a PLGA microsphere formulation, an oil suspension formulation, or an in-situ gel formulation of the invention described herein.

In some embodiments of the method of the invention, the injectable formulation of the invention can be used for a nerve block in post operative pain (e.g., knee surgery or shoulder surgery or any other surgery where a peripheral nerve block is standard of care to provide anesthesia). Such a formulation comprising Compound A, or a pharmaceutically acceptable salt thereof, has demonstrated the advantage of providing analgesia without paralyzing the muscles which would allow movement which is important after surgery.

It is reported that NaV 1.7 is present in cartilage and may be associated with disease modifying effects in osteoarthritis (as opposed to just analgesia). It is another aspect of the present invention that the formulation of the invention comprising Compound A can be used as an intraarticular injection (e.g., knee) for the treatment of pain due to osteoarthritis or due to focal peripheral neuropathic pain and potentially for its disease modifying effects (e.g., increases in cartilage volume), particularly when the release profile is prolonged.

In some embodiments of the method of the invention, the pain is a post operative pain associated with a nerve block. In some embodiments, the post operative pain associated with a nerve block is from a knee surgery, a shoulder surgery, or any other surgery where a peripheral nerve block is standard of care to provide anesthesia.

In some embodiments, the method of the invention provides analgesia without paralyzing the muscles.

In some embodiments of the method of the invention, the pain is due to osteoarthritis or due to focal peripheral neuropathic pain. In some embodiments, the focal peripheral neuropathic pain is caused by post-traumatic neuralgia, neuroma, post-amputation stump pain, meralgia paresthetica, or focal peripheral mononeuropathy. In some embodiments, the focal peripheral mononeuropathy is associated with diabetic neuropathy, chronic regional pain syndrome types 1 and 2, or post-herpetic neuralgia. In certain embodiments of the method of the invention, the administration in the method of the invention is by an intraarticular injection. In some embodiments, the intraarticular injection leads to a disease modifying effect on osteoarthritis. In some embodiments, the disease modifying effect on osteoarthritis comprises an increase in cartilage volume.

In some embodiments, the intraarticular injection will last for at least 20 days. In some embodiments, the intraarticular injection will last for at least 25 days. In some embodiments, the intraarticular injection will last for at least 30 days.

In some embodiments of the method of the invention, the pain is neuropathic, nociceptive or inflammatory pain.

In other embodiments, the pain is nociceptive pain, such as that resulting from physical trauma (e.g., a cut or contusion of the skin including surgery or dental pain; or a chemical or thermal burn), osteoarthritis, rheumatoid arthritis or tendonitis; myofascial pain; neuropathic pain, such as that associated with stroke, diabetic neuropathy, luetic neuropathy, postherpetic neuralgia, trigeminal neuralgia, fibromyalgia, or painful neuropathy induced iatrogenically by drugs; or mixed pain (e.g., pain with both nociceptive and neuropathic components); visceral pain; headache pain (e.g., migraine headache pain); complex regional pain syndrome ("CRPS"); CRPS type I; CRPS type II; reflex sympathetic dystrophy ("RSD"); reflex neurovascular dystrophy; reflex dystrophy; sympathetically maintained pain syndrome; causalgia; Sudeck atrophy of bone; algoneurodystrophy; shoulder hand syndrome; post-traumatic dystrophy; autonomic dysfunction; autoimmune-related pain; inflammation-related pain; cancer-related pain; phantom limb pain; chronic fatigue syndrome; post-operative pain; spinal cord injury pain; central post-stroke pain; radiculopathy; sensitivity to temperature, light touch or color change to the skin (allodynia); pain from hyperthermic or hypothermic conditions; and other painful conditions (e.g., diabetic neuropathy, luetic neuropathy, postherpetic neuralgia, trigeminal neuralgia); chronic pain; acute pain; pain from neuromas, pain or itch associated with channelopathies such as small fiber neuralgia, inherited erythromelalgia ("IEM"), or Reynaud's; or itch from various origins such as allergic itch.

In some embodiments of the method of the invention, the pharmaceutical injectable formulation is an aqueous suspension formulation comprising about 50 mg/mL Compound A or a HCl salt of Compound A, about 0.5% (w/w) poloxamer 188, about 1% (w/w) CMC-Na, about 0.6% (w/w) NaCl, a pH of about 7.4 in about 20 mM phosphate buffer. In some embodiments, the formulation comprises a HCl salt of Compound A. In certain embodiments, the formulation comprises Compound A.

In some embodiments of the method of the invention, the pharmaceutical injectable formulation is a PLGA microsphere formulation comprising about 20 mg/mL Compound A or a HCl salt of Compound A, poly(Lactic-co-Glycolic Acid (PLGA), about 1% (w/w) CMC-Na, about 1.5% (w/w) mannitol, and a pH of about 7.4 in about 20 mM phosphate buffer, wherein the weight ratio of Compound A to PLGA is about 1:2. In some embodiments, the formulation comprises a HCl salt of Compound A. In certain embodiments, the formulation comprises about 20 mg/mL Compound A.

In some embodiments of the method of the invention, the pharmaceutical injectable formulation is an oil suspension formulation comprising about 50 mg/mL Compound A or a HCl salt of Compound A and benzyl benzoate in sesame oil, wherein the concentration of benzyl benzoate is about 20% (v/v). In some embodiments, the formulation comprises a HCl salt of Compound A. In certain embodiments, the formulation comprises Compound A.

In some embodiments of the method of the invention, the pharmaceutical injectable formulation is an in-situ gel formulation comprising about 100 mg/mL Compound A or a HCl salt of Compound A, about 24.40% (w/w) NMP, about 26.4% (w/w) soy lecithin, and 39.6% (w/w) glycerin dioleate. In some embodiments, the formulation comprises a HCl salt of Compound A. In certain embodiments, the formulation comprises Compound A.

As used herein, the terms "treating" or "treatment" includes preventative as well as disorder remitative treatment. The terms "reducing" and "alleviating" have their commonly understood meaning of lessening or decreasing, or delaying, or reducing, the incidence, severity or pathogenesis of a disease, disorder or condition. In one embodiment, the term treatment refers to delayed progression of, prolonged remission of, reduced incidence of, or amelioration of symptoms associated with the disease, disorder or condition. In one embodiment, the terms "treating", "reducing", or "alleviating" refer to a reduction in morbidity, mortality, or a combination thereof, in association with the indicated disease, disorder or condition. In one embodiment, the methods of treatment disclosed herein reduce the severity of the disease, or in another embodiment, symptoms associated with the disease, or in another embodiment, reduces the number of biomarkers expressed during disease.

As used herein, the term "a therapeutically effective amount" of a compound, e.g., Compound A, or a pharmaceutically acceptable salt thereof, means an amount of the compound that is effective to prevent, alleviate, or treat pain. Determination of a therapeutically effective amount is within the skill in the art. The therapeutically effective amount or dosage of a compound according to this invention can vary within wide limits and may be determined in a manner known in the art. In cases of administration of a pharmaceutically acceptable salt, dosages may be calculated as the free base.

The exact dose and regimen of administration of the composition will necessarily be dependent upon the therapeutic or nutritional effect to be achieved and may vary with the particular formula, the route of administration, and the age and condition of the individual subject to whom the composition is to be administered. Administration of the formulations of the invention may for example be intravenous, intra-arterial, intrathecal, intramuscular, subcutaneous, intramuscular, intra-abdominal (e.g., intraperitoneal), etc.

In one embodiment, the term "administering" refers to bringing a subject, e.g., a mammal (e.g., a human or non-human mammal) in contact with a pharmaceutical formulation of the present disclosure.

In some embodiments, the term "about" refers to a variation of 0.0001-5% from the indicated number or range of numbers. In one embodiment, the term "about" refers to a variation of 0.0001-1% from the indicated number or range of numbers. In one embodiment, the term "about" refers to a variation of 1-10% from the indicated number or range of numbers. In one embodiment, the term "about" refers to a variation of up to 25% from the indicated number or range of numbers.

Select abbreviations and acronyms:
- sodium carboxymethylcellulose (CMC-Na)
- hydroxypropyl methylcellulose (HPMC)
- hydroxypropyl beta cyclodextrin (HPBCD)
- polysorbate (PS)
- phosphate buffer (PB)
- polyethylene glycol (PEG)
- sulfobutylether-β-cyclodextrin (SBECD)
- cyclodextrins (CD)
- poly(lactic-co-glycolic acid) (PLGA)
- N-methylpyrrolidone (NMP)

Throughout this application, various embodiments of the present disclosure may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicated number and a second indicated number and "ranging/ranges from" a first indicated number "to" a second indicated number are used herein interchangeably and are meant to include the first and second indicated numbers and all the fractional and integral numerals therebetween.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting. Each literature reference or other citation referred to herein is incorporated herein by reference in its entirety.

In the description presented herein, each of the steps of the invention and variations thereof are described. This description is not intended to be limiting and changes in the components, sequence of steps, and other variations would be understood to be within the scope of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Example 1: Injectable Formulations of Invention

This study aims to develop a peripheral nerve injection formulation of 20 mg/mL or above of CC8464 HCl that can sustain release for 96 hours (3~5 days).

Results:

CC8464 HCl is a highly crystalline white solid with a molecular weight of 569.88. The solubility of both CC8464 HCl salt and free base is poor in aqueous and oil phases, less than 5 mg/mL. The solubility of CC8464 HCl salt exceeds that of the CC8464 free base in the presence of surfactants and polymers, reaching 3.7 mg/mL in 1% PS20. Both forms exhibit good solubility in organic phases like DMSO, DMF, and NMP, exceeding 200 mg/mL. The CC8464 free base also shows a solubility greater than 200 mg/mL in benzyl alcohol.

After jet milling, the crystal form of CC8464 HCl salt and free base remains the same, but the particle size is significantly reduced to a $D_{90}$ of less than 15 μm.

Feasibility studies were conducted on six formulations, including micro-suspension, PLGA microspheres, injectable emulsion, liposomes, oil-based suspension, and in situ gel. Of these, suitable formulations were identified for four, detailed as follows:

Aqueous Suspension

CC8464 HCl salt (50 mg/mL) in 20 mM phosphate buffer pH 7.4+0.5% P188+1% CMC-Na+0.6% NaCl with final pH around 7.4.

PLGA Microsphere

CC8464 free base (50 mg/mL): PLGA=1:2, the diluent is 20 mM phosphate buffer pH 7.4+1% CMC-Na+1.5% mannitol with final pH around 7.4.

Oil Suspension 50 mg/mL CC8464 HCl salt in sesame oil: Benzyl benzoate (80:20, v/v).

In Situ Gel 100 mg/mL CC8464 HCl salt (9.5 wt %), 24.40 wt % NMP, and soy lecithin/glycerin dioleate in weight ratio 40/60 to final volume.

TABLE 1

Injectable Formulation composition

| Formulation type | | Component | Concentration (mg/mL) | Description |
|---|---|---|---|---|
| Aqueous suspension (F1) | Vial A | CC8464 HCl salt | 50.00 | Active ingredient |
| | Vial B | Poloxamer 188 | 5.00 | Surfactant |
| | | Sodium carboxymethylcellulose (CMC-Na) | 10.00 | Suspension |
| | | Disodium hydrogen phosphate dihydrate | 2.68 | Buffer |
| | | Sodium dihydrogen phosphate dihydrate | 0.77 | Buffer |
| | | Sodium chloride (NaCl) | 6.00 | Osmolality adjuster |
| | | Water for injection (WFI) | q.s. | Solvent |
| | | Sodium hydroxide (NaOH) | q.s. | pH adjuster |
| | | Hydrochloric acid (HCl) | q.s. | pH adjuster |
| PLGA microspheres (F2) | Vial A | CC8464 free base | 50.00 | Active ingredient |
| | | Poly(lactic-co-glycolic) acid (PLGA) 50:50 | 100.00 | Carrier |
| | | Disodium hydrogen phosphate dihydrate | 1.34 | Buffer |
| | | Sodium dihydrogen phosphate dihydrate | 0.38 | Buffer |
| | | Mannitol | 20.00 | Lyoprotectant |
| | Vial B | Sodium carboxymethylcellulose (CMC-Na) | 10.00 | Suspension |
| | | Disodium hydrogen phosphate dihydrate | 1.34 | Buffer |
| | | Sodium dihydrogen phosphate dihydrate | 0.38 | Buffer |
| | | Mannitol | 15.00 | Osmolality adjuster |
| | | Water for injection (WFI) | q.s. | Solvent |
| | | Sodium hydroxide (NaOH) | q.s. | pH adjuster |
| | | Hydrochloric acid (HCl) | q.s. | pH adjuster |
| Oil suspension (F3) | | CC8464 HCl salt | 50.00 | Active ingredient |
| | | Sesame oil | 800.00 | Oil phase |
| | | Benzyl benzoate | 200.00 | Preservative |
| In-situ gel (F4) | | CC8464 HCl salt | 100.00 | Active ingredient |
| | | NMP | 257.00 | Solvent |
| | | Soy lecithin | 278.50 | Matrix |
| | | Glycerin dioleate | 417.50 | Matrix |

Example 2: Preparation of Formulations

Formula F1 (CC8464 HCl Salt in 20 mM PB pH 7.4+0.5% P188+1% CMC-Na+0.6% NaCl)

API jet milling parameter: Injector gas pressure: 4 bar; Grinding gas pressure: 3.5 bar.

Vial a (CC8464 HCl Salt, 60 mg API/Vial)

About 60 mg of CC8464 HCl salt after jet milling was weighed into 2R vials (60 mg API/vial).

Vial B (0.5% P188+1% CMC-Na+0.6% NaCl in 20 mM PB pH 7.4, 1.2 mL/Vial)

To prepare vehicle at a batch size of 300 mL, 1.5 g of Poloxamer P188, 3 g of CMC-Na, 804 mg of $Na_2HPO_4 \cdot 2H_2O$, 231 mg of $NaH_2PO_4 \cdot 2H_2O$, 1.8 g of NaCl and water were mixed to target volume, pH was adjusted to 7.4 with 1 N HCl or 1 N NaOH. The vehicle was filtrated by 0.22 μm filter and filled into 2R vials (about 1.2 mL/vial).

CC8464 HCl salt aqueous suspension: To prepare CC8464 HCl salt aqueous suspension at 50 mg/mL, vial A was re-suspended with 1.1 mL of vial B and sonicated for 1-2 min.

Formulation F2 (CC 8464 Free Base PLGA Microspheres in 20 mM PB pH 7.4+1% CMC-Na+3.5% Mannitol)

Vial A (CC8464 PLGA Microsphere Lyophilized Powder, 60 mg API/Vial):

To prepare CC8464 PLGA microsphere at 50 mg/mL at a batch size of 200 mL, following steps were conducted:

1. Oil phase preparation: About 1800 mg of CC8464 free base and 3600 mg of PLGA were dissolved by 180 mL of DCM: DMF=1:1.
2. The oil phase was added into 3600 mL of water phase (1% PVA+0.9% NaCl in 20 mM PB pH 8) and mixed by homogenizer at 10000 rpm for 5 min (room temperature). Then the mixture was mixed by microfluidics at 5000 psi for 1 cycle.
3. After step 2, DCM was removed by rotary evaporation at 100 rpm, 30 C for 1 h (200-300 mbar).
4. After step 3, the mixture was diluted with 20 mM PB pH 7.4 for 2× and centrifuged at 4000 rpm for 5 min, the supernatant was removed.
5. The residual solid was re-suspended with 10 mM PB pH 7.4 centrifuged at 4000 rpm for 5 min, the supernatant was removed. Repeat this step for 2 times.
6. Formulation preparation: The residual solid of step 5 was re-suspended with 10% mannitol, 20 mM PB pH 7.4 and water to target 50 mg/mL in 2% mannitol+10 mM PB pH 7.4.
7. The formulation was filled into 2R vials (about 60 mg API/vial) and freeze-dried.

Vial B (1% CMC-Na+1.5% Mannitol in 10 mM PB pH 7.4, 1.2 mL/vial):

To prepare vehicle at a batch size of 300 mL, 3 g of CMC-Na, 402 mg of $Na_2HPO_4 \cdot 2H_2O$, 115.5 mg of $NaH_2PO_4 \cdot 2H_2O$, 4.5 g of mannitol and water were mixed to target volume, pH was adjusted to 7.4 with 1N HCl or 1N NaOH. The vehicle was filtrated by 0.22 μm filter and filled into 2R vials (about 1.2 mL/vial).

CC8464 PLGA Microsphere:

To prepare CC8464 PLGA microsphere at 50 mg/mL, vial A was re-suspended with 1.1 mL of vial B and sonicated for 1-2 min.

Formulation F3: 50 mg/mL CC8464 HCl in Sesame Oil: Benzyl Benzoate (80:20, v/v)

1. API jet milling parameter: Injector gas pressure: 4 bar; Grinding gas pressure: 3.5 bar.
2. Prepare a 150 mL formulation batch by adding 120 mL of sesame oil, 30 mL of benzyl benzoate, and 7.7 g of CC8464 HCl salt.
3. Homogenize at 10900 rpm for 3 minutes to obtain a uniform oil suspension sample.
4. Divide the sample into 2R vials using a pipette, with 2 mL per vial.

Formulation F4 (100 mg/mL CC8464 HCl in Soy Lecithin: Glycerin Dioleate (4:6, w/w))

CC8464-HCl: 200 mg (9.5 wt %)
NMP: 0.514 g (24.4 wt %)
Soy lecithin: 0.557 g (26.4 wt %)
Glycerin dioleate: 0.835 g (39.6 wt %)

To prepare CC8464 in situ gel at 100 mg/mL at a batch size of ~200 mL, following steps were conducted:

1. API solution: 24 g CC8644-HCl was dissolved in 61.68 g NMP (~60 mL) and stirred at 700 rpm for about 20 min until the compound was completely dissolved.
2. 66.84 g SPC was dissolved in API solution and stirred at 45° C. at 700 rpm for about 2 hours until completely dissolved.
3. 100.2 g GDO was added into the sample solution and stirred at 700 rpm for about 15 min to make it evenly mixed.
4. The gel solution was filtered through a 0.2 μm PTFE filter and packed into 2R vials.

Example 3: PK Studies

Table 2 provides PK results for formulations of the invention. In Table 2, Column B contains the 4 different formulations. Column D and E contain the dose administered to the animal (Rat). Column F contains the formulation details. Column G contains the time points that were measured in this initial trial. Column H contains the plasma concentration (blood) (P is abbreviation for Plasma).

Columns I-L contain the muscle concentration from the area immediately adjacent to the injection site. For example, ScN_R is abbreviation for Sciatic Nerve (Right); M_1_R is abbreviation for Muscle from injection area (Right); M_2_R is abbreviation for Muscle from 1 cm distant from the injection site (Right); M_3_R is abbreviation for Muscle from 2 cm distant from the injection site (Right); and M_4_L is abbreviation for Muscle from the contralateral (Left).

Column M contains the sciatic nerve concentration. The injection was into the perineural space, immediately adjacent to the sciatic nerve. It is shown that a gradient is created with high concentrations near the nerve and adjacent muscles with progressively lower concentrations as it is moved further away from the injection site. This demonstrates that a depot effect has been created that could be useful for nerve blocks.

TABLE 2

PK Study Results

| D Nominal dose (mg/animal) | E Administered dose (mg/animal) | F Formulation | G Time (h) | H Plasma concentration (ng/mL) | I Muscle 1-R concentration (ng/g) | J Muscle 2-R concentration (ng/g) | K Muscle 3-R concentration (ng/g) | L Muscle 4-L concentration (ng/g) | M Sciatic nerve concentration (ng/g) |
|---|---|---|---|---|---|---|---|---|---|
| 10.0 | 8.00 | 50 mg/mL in F1: CC8464 HCl salt aqueous suspension, homogenous opaque suspension | 12 | 357 | 8264579 | 19100 | 2458 | 659 | 161858 |
| | | | 24 | 318 | 7364912 | 10874 | 2385 | 439 | 32774 |

TABLE 2-continued

| PK Study Results | | | | | | | | | |
|---|---|---|---|---|---|---|---|---|---|
| D Nominal dose (mg/animal) | E Administered dose (mg/animal) | F Formulation | G Time (h) | H Plasma concen-tration (ng/mL) | I Muscle 1-R concen-tration (ng/g) | J Muscle 2-R concen-tration (ng/g) | K Muscle 3-R concen-tration (ng/g) | L Muscle 4-L concen-tration (ng/g) | M Sciatic nerve concen-tration (ng/g) |
| 10.0 | 10.4 | 50 mg/mL in F2: CC8464 free base PLGA microspheres, homogenous opaque suspension | 12 | 250 | 9782070 | 9565 | 1938 | 295 | 32065 |
| | | | 24 | 72.4 | 8539892 | 2547 | 847 | 323 | 83971 |
| 10.0 | 9.49 | 50 mg/mL in F3: CC8464 HCl salt Oil suspension, homogenous opaque suspension | 12 | 512 | 8267304 | 61316 | 3143 | 322 | 185422 |
| | | | 24 | 289 | 2643193 | 13211 | 2908 | 234 | 94529 |
| 10.0 | 8.86 | 100 mg/mL in F4: CC8464 HCl-In situ gel, clear solution | 12 | 422 | 1175937 | 11376 | 3558 | 471 | 185035 |
| | | | 24 | 328 | 661834 | 73184 | 3162 | 311 | 20479 |

Example 4: Sciatic Nerve Block Assay in Mice

This study was to evaluate the efficacy of test articles in sciatic nerve block assay in C57 mice.

TABLE 3

| Animals model | |
|---|---|
| Animal Species | mouse |
| Strain | C57 |
| Body weight | 20-23 g |
| Sex | male |

TABLE 4

| Drugs or compounds used in assay | | | |
|---|---|---|---|
| Compound ID | Appearance | Concentration (mg/mL) | Storage |
| Bupivacaine | Colorless clarified solution | 7.5 (0.75%) | Room temperature |
| CC8464 free base PLGA microspheres (Formulation 1) | White cake | 50 | 2-8° C. |
| CC8464 HCl salt aqueous suspension (Formulation 2) | White powder | 50 | 2-8° C. |
| CC8464 HCl salt Oil suspension (Formulation 3) | Suspension | 50 | 2-8° C. |
| CC8464 HCl-In situ gel (Formulation 4) | Yellow clarified solution | 100 | −20° C. |

TABLE 5

| Experimental Groups/Animal Groups | | | | | | | |
|---|---|---|---|---|---|---|---|
| Group | Treatment | Dose (mg/mL) | Solution | Dose volume (μL/animal) | N | Dose route | Test |
| 1 | Vehicle | — | saline | 100 | 10 | sciatic nerve infiltration | Thermal hyperalgesia tests of all group |

TABLE 5-continued

| Experimental Groups/Animal Groups | | | | | | | |
|---|---|---|---|---|---|---|---|
| Group | Treatment | Dose (mg/mL) | Solution | Dose volume (μL/animal) | N | Dose route | Test |
| 2 | Bupivacaine | 3 (0.3%) | saline | 100 | 10 | sciatic nerve infiltration | animals were performed by using Plantar Tester (IR = 50, cut off = 15 s) twice a day for 5 days after dosing, 4 hours apart every day. The test timepoints were as follows: 0.5 h, 4.5 h, 24 h, 28 h, 48 h, 52 h, 72 h, 76 h, 96 h, 100 h. |
| 3 | CC8464, Formulation 1 | 50 | — | 100 | 10 | sciatic nerve infiltration | |
| 4 | CC8464, Formulation 2 | 50 | — | 100 | 10 | sciatic nerve infiltration | |
| 5 | CC8464, Formulation 3 | 50 | — | 100 | 10 | sciatic nerve infiltration | |
| 6 | CC8464, Formulation 4 | 100 | — | 100 | 10 | sciatic nerve infiltration | |

Timelines: two weeks

TABLE 6

| Bupivacaine information | | | | | | |
|---|---|---|---|---|---|---|
| | Concentration | | 0.75% Bupivacaine | Saline | | Preparation |
| Drug | (%) | (mg/mL) | (mL) | (mL) | Method | time |
| Bupivacaine | 0.30% | 3 | 0.5 | 0.75 | Absorb 0.5 mL of 0.75% bupivacaine solution, add 0.75 mL saline, swirl and mix to obtain 0.3% bupivacaine solution. | day 1 |

TABLE 7

| Compound information | | | | | |
|---|---|---|---|---|---|
| Compound Name | Conc. (mg/mL) | Vial A | Vial B | Method | Preparation time |
| CC8464 free base PLGA microspheres (Formulation 1) | 50 | CC8464 PLGA microspheres + 2% mannitol in 10 mM PB pH 7.4 (CC8464: 60 mg) | 10 mM PB pH 7.4 + 1% CMC-Na + 1.5% Mannitol (1.2 mL) | This formulation is composed of vial A and vial B, mixed well before use. | day 0 |
| CC8464 HCl salt aqueous suspension (Formulation 2) | 50 | CC8464 HCl salt (60 mg) | 20 mM PB pH 7.4 + 0.5% P188 + 1% CMC-Na + 0.6% NaCl (1.2 mL) | This formulation is composed of vial A and vial B, mixed well before use. | day 0 |
| CC8464 HCl salt Oil suspension (Formulation 3) | 50 | — | — | — | day 1 |
| CC8464 HCl-In situ gel (Formulation 4) | 100 | — | — | — | day 1 |

Animal Procedures

Acclimation: The animals were acclimatized for 3 days after arrival at the facility. Three days prior to dosing, all mice were acclimated to thermal hyperalgesia (PWL) test for 30 min per day.

Group setting: PWL test was performed on all animals twice by Plantar Tester before dosing, and the average value of two results were taken as PWL value of the animal. Those animals with PWL more than 8s were eliminated. Animals were randomly divided into 6 groups based on PWL baseline, 10 animals in each group.

Sciatic nerve block: Dosing in the peripheral space of the sciatic nerve on the left side of the animal.

Thermal hyperalgesia test at different timepoints after dosing: Thermal hyperalgesia test of all group animals was performed by using Plantar Tester twice a day for 5 days after dosing, 4 hours apart every day. The test timepoints were as follows: 0.5 h, 4.5 h, 24 h, 28 h, 48 h, 52 h, 72 h, 76 h, 96 h, 100 h.

Method of Thermal Hyperalgesia Test

Before the thermal hyperalgesia test, the mice were placed in a plexiglass box which was placed on a special glass plate and acclimated to test environment for about 10 minutes until they were quiet.

The Ugo Basile Plantar Tester was used to focus the radiant heat source through the glass surface to the plantar region of the paw of mice, with IR set to 50, and recorded the time it took the mouse to remove its paw from the heat source, known as the paw withdrawal latency (PWL).

To avoid tissue damage, every test had a cutoff time of up to 15 s (Cutoff value), and this test was terminated even if the animal did not remove its paw from the thermal stimulation. For mice that did not shrink their feet within the set time (15 s), the paw withdrawal latency was denoted as 15s.

A test for efficacy of compound at one timepoint consisted of two tests of the same paw, at least 3 minutes apart between each test, and the average value of two results was taken as PWL value of the mouse.

Time frame as shown in FIG. 5A (Scheme 1).

Termination procedure: Animals were euthanized with $CO_2$ at the end of the study.

Results

FIG. 1 provides thermal hyperalgesia test results. In FIG. 1, data were presented as mean±SEM, n=10/group. * p<0.05,  p<0.01, * p<0.001 vs. vehicle group by two-way ANOVA followed by Dunnett's multiple comparisons test. Analgesia (% MPE)=(value of dosing group-average value of vehicle group)/(15-average value of vehicle group)*100%.

Figure 2:
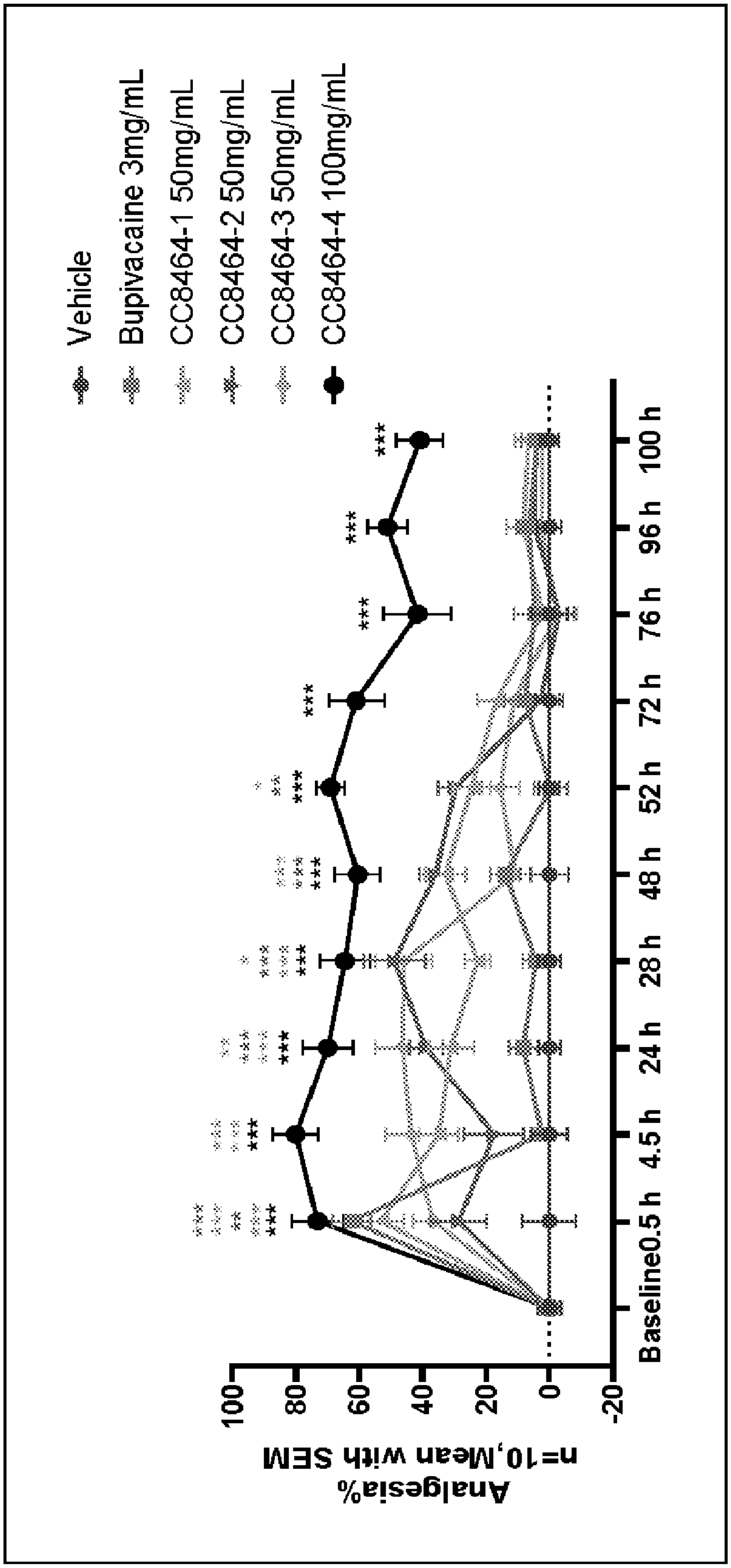
FIG. 2 depicts analgesia % results in Example 4.

FIG. 2 provides analgesia % results. In FIG. 2, Data were presented as Mean±SEM, n=10/group. * p<0.05,  p<0.01, * p<0.001 vs. vehicle group by two-way ANOVA followed by Dunnett's multiple comparisons test.

Example 5: Evaluation in Post-Surgery Pain in Mice

This study was to evaluate the efficacy of test article in post-surgery pain model in C57 mice.

TABLE 8

| Animal Model | |
|---|---|
| Animal Species | mouse |
| Strain | C57 |
| Body weight | 18-22 g |
| Sex | male |

TABLE 9

| Treatment Group | | | | | | | |
|---|---|---|---|---|---|---|---|
| Group | Treatment | Dose (mg/mL) | Solution | Dose volume (μL/animal) | Dosing route | N | Testing timepoints |
| 1 | Vehicle | — | saline | 100 | sciatic nerve infiltration | 10 | 0.5 h, 4.5 h, 24 h, 28 h, 48 h, 52 h |
| 2 | Bupivacaine | 1.5 (0.15%) | saline | 100 | sciatic nerve infiltration | 10 | |
| 3 | CC8464, formulation 1 | 50 | — | 100 | sciatic nerve infiltration | 10 | |
| 4 | CC8464, formulation 2 | 50 | — | 100 | sciatic nerve infiltration | 10 | |
| 5 | CC8464, formulation 3 | 50 | — | 100 | sciatic nerve infiltration | 10 | |
| 6 | CC8464, formulation 4 | 100 | — | 100 | sciatic nerve infiltration | 10 | |

TABLE 10

| Compound Information | | | | |
|---|---|---|---|---|
| Compound | Appearance | Concentration (mg/mL) | Storage | Preparation |
| Bupivacaine | Colorless clarified solution | 7.5 (0.75%) | Room temperature | Absorb an appropriate amount of 0.75% bupivacaine solution, add the corresponding volume of normal saline, swirl and mix to obtain 0.15% bupivacaine solution |
| CC8464 free base PLGA microspheres (formulation 1) | White cake | 50 | 2-8° C. | This formulation is composed of vial A and vial B, mixed well before use. Vial A: CC8464 PLGA microspheres + 2% mannitol in |

TABLE 10-continued

| Compound Information | | | | |
|---|---|---|---|---|
| Compound | Appearance | Concentration (mg/mL) | Storage | Preparation |
| | | | | 10 mM PB pH 7.4 (CC8464: 60 mg) Vial B: 10 mM PB pH 7.4 + 1% CMC-Na + 1.5% Mannitol (1.2 mL) |
| CC8464 HCl salt aqueous suspension (formulation 2) | White powder | 50 | 2-8° C. | This formulation is composed of vial A and vial B, mixed well before use. Vial A: CC8464 HCl salt (60 mg) Vial B: 20 mM PB pH 7.4 + 0.5% P188 + 1% CMC-Na + 0.6% NaCl (1.2 mL) |
| CC8464 HCl salt Oil suspension (formulation 3) | Suspension | 50 | 2-8° C. | |
| CC8464 HCl-In situ gel (formulation 4) | Yellow clarified solution | 100 | −20° C. | |

Animal Procedures

Acclimation: The animals were acclimatized for 3 days after arrival at the facility. Three days prior to modeling, all mice were acclimated to mechanical allodynia test with a same test filament.

Post-Surgery Pain Model

Animals were anesthetized with Zoletil 50 (50 mg/kg, 2 mL/kg, i.p.) and Xylazine Hydrochloride (8 mg/kg, 2 mL/kg, i.p.). A toe pinch was used to ensure that the animals were fully anesthetized prior to any incision. Ophthalmic ointment was put in the rodent's eyes to prevent the corneas from drying out.

The plantar aspect of the left hind paw was swabbed with 3 rounds of alternating Betadine and 70% ethanol.

A 5-mm longitudinal incision was made through the skin and fascia, starting 2 mm from the proximal edge of the heel and extending towards the toes, the plantar muscle was elevated and injured longitudinally leaving the muscle origin and insertion points intact.

After hemostasis with gentle pressure, the skin was apposed with two mattress sutures.

Animals were allowed to recover from anesthesia on a warm recovery pad. Subcutaneously 1 mL sterile saline was injected to prevent dehydration during the post-operative recovery period. The animals were then returned to their home cages after fully awake (walking around).

Group Setting: 24 hours after surgery, all animals were tested for mechanical allodynia (PWT) by Touch-Test Sensory Evaluator. Surgical animals that didn't exhibit allodynia (PWT>0.6 g) would be eliminated, then the qualified surgical animals would be randomly divided into 6 groups based on PWT baseline, 10 animals in each group.

Dosing: After animals were anesthetized with isoflurane, the animals were dosed in the peripheral space of the sciatic nerve on the left side.

Mechanical allodynia test at different timepoints after dosing: Mechanical allodynia test of all group animals was performed by using Von Frey filaments for 3 days after dosing, 4 hours apart every day. The test timepoints were as follows: 0.5 h, 4.5 h, 24 h, 28 h, 48 h, 52 h.

Method of Mechanical Allodynia Test

Mice were placed individually in a plastic enclosure with a mesh bottom, which allowed full access to the paws and acclimated for 15 minutes before mechanical allodynia measurement.

After acclimation, the left mid-plantar hind paw of rat was touched with one of a series of eight von Frey hairs with logarithmically incremental stiffness as follows: 2.36 (0.02 g), 2.44 (0.04 g), 2.83 (0.07 g), 3.22 (0.16 g), 3.61 (0.4 g), 3.84 (0.6 g), 4.08 (1 g), 4.17 (1.4 g). The von Frey hairs were presented perpendicularly to the plantar surface with sufficient force to cause slight buckling against the paw and held for approximately 6-8 s. Stimulation was presented at intervals of 5 seconds, allowing for apparent resolution of any behavioral responses to previous stimulus. A positive response would be noted if the paw was sharply withdrawn. Flinching immediately upon removal of the hair was also considered as a positive response. Ambulation was considered as an ambiguous response, and in such cases, the stimulus was repeated.

Starting with filament 3.22 (0.16 g), depending on response or no response, the investigator used a filament of decreasing or increasing force, respectively, based on Dixon up-down method. Positive responses included an obvious withdrawal of the hind paw from the filament, or flinching behavior immediately following removal of the filament. The maximum force applied was filament 4.17 (1.4 g).

Mechanical allodynia was calculated and expressed using the formula:

$$50\ \%\ \text{response threshold (g)} = \left(10^{(Xf+k\delta)}\right)/10{,}000$$

Xf=value (in log units) of the final von Frey filament used

δ=mean difference (in log units) between stimuli (0.259)

k=tabular value for the pattern of positive/negative responses

Time Frame as shown in FIG. 5B (Scheme 2).

Termination procedure: Animals were euthanized with $CO_2$ at the end of the study.

Results

Figure 3:
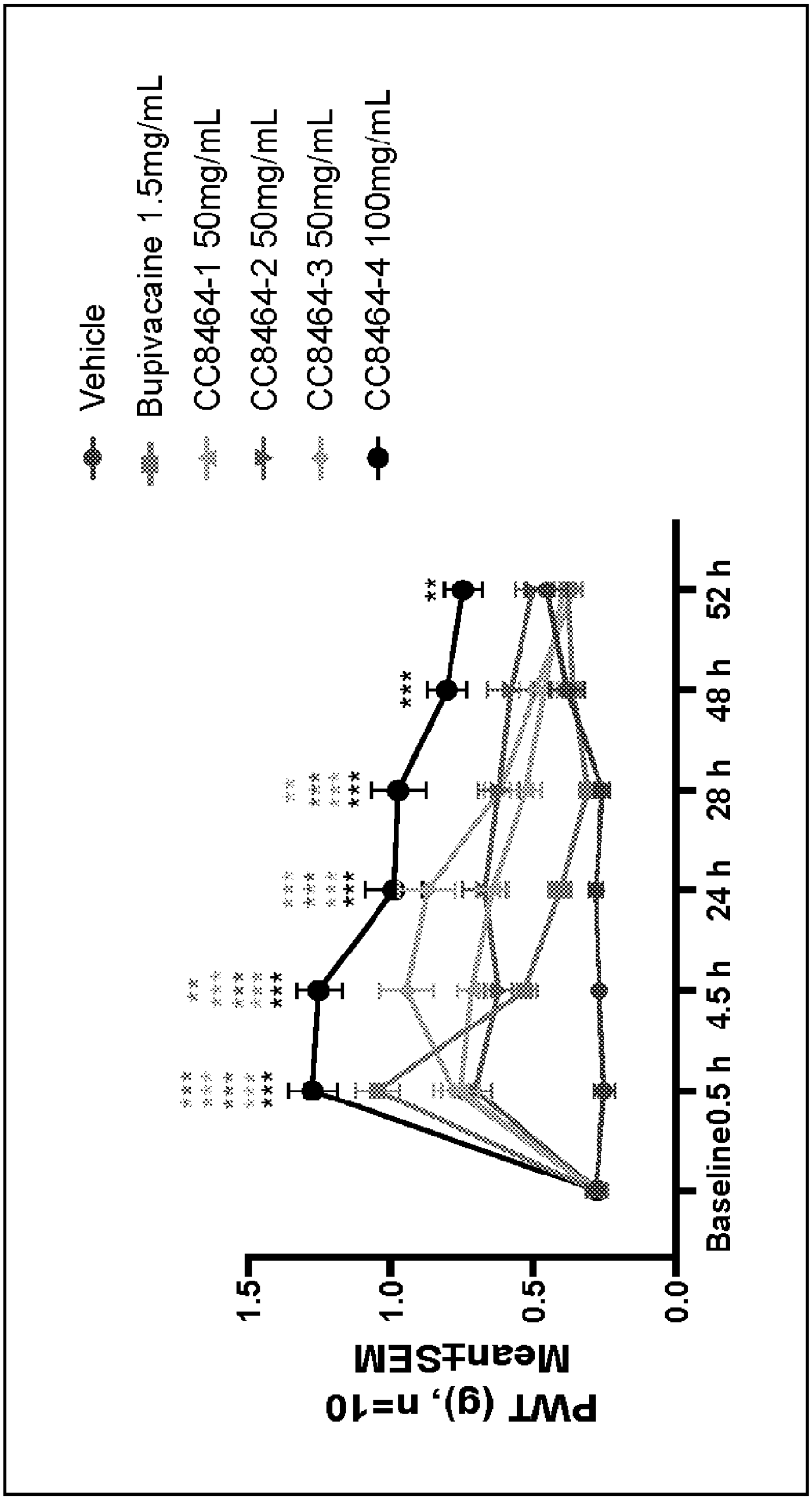
FIG. 3 depicts PWT results in Example 5.

FIG. 3 provides PWT results, where data were presented as mean±SEM, n=10/group. * p<0.05,  p<0.01, * p<0.001 vs. vehicle group by two-way ANOVA followed by Dunnett's multiple comparisons test.

Figure 4:
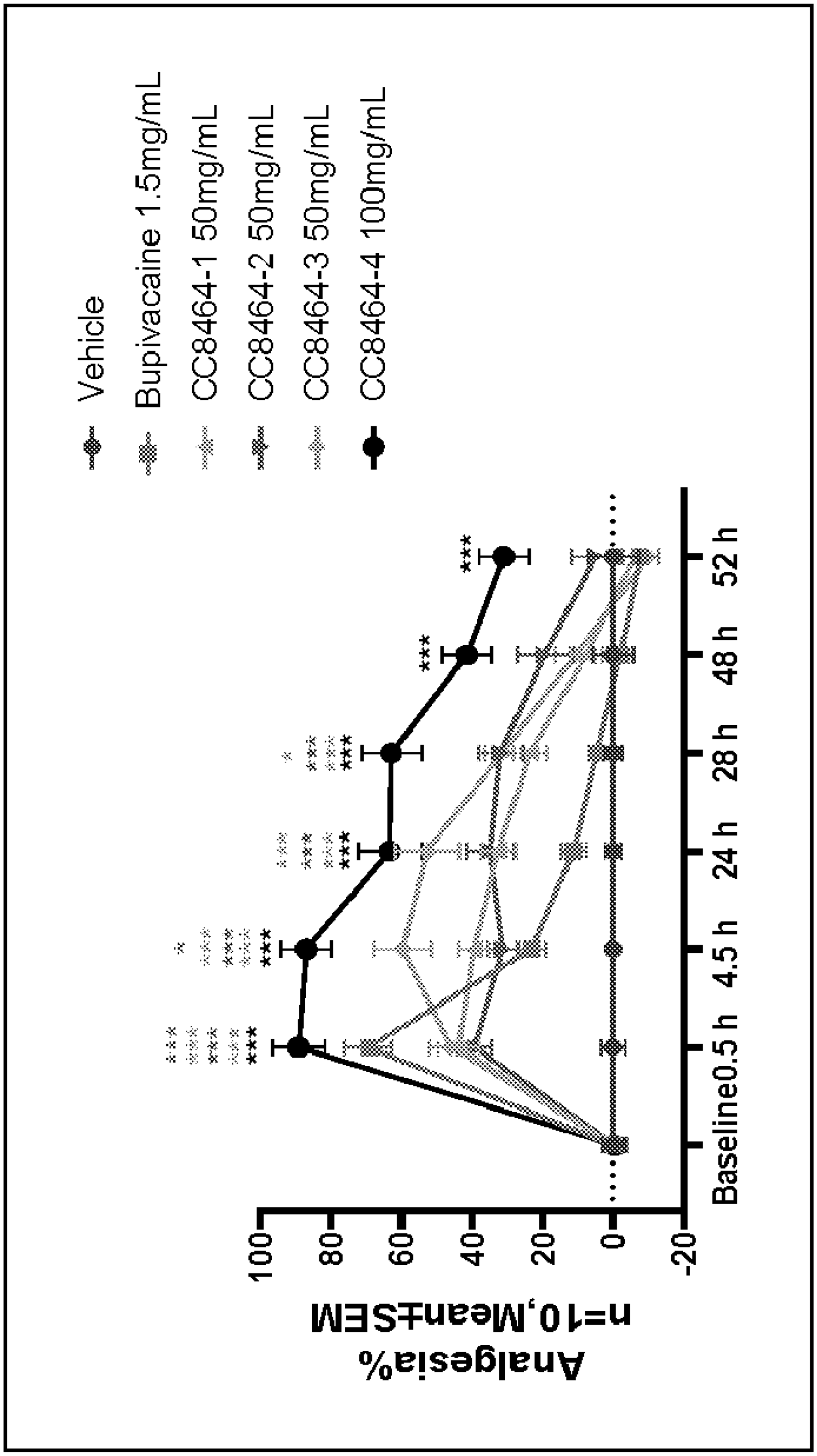
FIG. 4 depicts analgesia results in Example 5.

FIG. 4 provides analgesia results, where data were presented as mean±SEM, n=10/group. * p<0.05,  p<0.01, * p<0.001 vs. Vehicle group by two-way ANOVA followed by Dunnett's multiple comparisons test. Analgesia (% MPE)=(value of dosing group-average value of vehicle group)/(1.4-average value of vehicle group)*100%.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed:

1. An oil suspension formulation comprising about 50 mg/mL Compound A or a HCl salt of Compound A and benzyl benzoate in sesame oil, wherein the concentration of benzyl benzoate is about 20% (v/v)

(A)

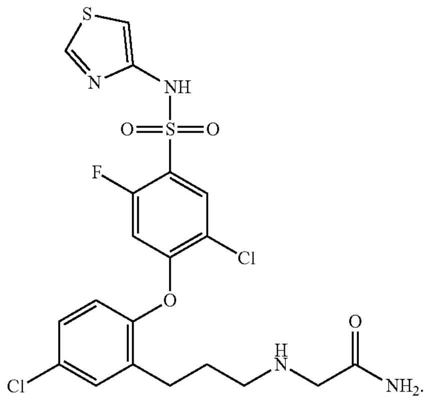

2. A method for treating or alleviating pain or providing peri-operative anesthesia or post-operative analgesia comprising administering to a subject in need thereof a therapeutically effective amount of an oil suspension formulation according to claim 1.

3. The method according to claim 2, wherein the pain is neuropathic, nociceptive or inflammatory or wherein the pain is a post operative pain associated with a nerve block.

4. The method according to claim 3, wherein the post operative pain associated with a nerve block is from a knee surgery, shoulder surgery, or any other surgery where a peripheral nerve block is standard of care to provide anesthesia.

5. The method according to claim 2, wherein the method provides analgesia without paralyzing the muscles.

6. The method according to claim 2, wherein the pain is due to osteoarthritis or due to focal peripheral neuropathic pain, wherein the focal peripheral neuropathic pain is caused by post-traumatic neuralgia, neuroma, post-amputation stump pain, meralgia paresthetica, focal peripheral mononeuropathy associated with diabetic neuropathy, chronic regional pain syndrome types 1 and 2, or post-herpetic neuralgia.

7. The method according to claim 2, wherein the pain is osteoarthritis pain, wherein the administration is by an intraarticular injection, wherein the intraarticular injection leads to a disease modifying effect on osteoarthritis, and wherein the disease modifying effect on osteoarthritis comprises an increase in cartilage volume.

* * * * *